United States Patent
Ein-Gal

(10) Patent No.: US 8,220,995 B2
(45) Date of Patent: Jul. 17, 2012

(54) UPRIGHT RADIATION TISSUE IMMOBILIZER

(76) Inventor: Moshe Ein-Gal, Ramat Hasharon (IL)

( * ) Notice: Subject to any disclaimer, the term of this patent is extended or adjusted under 35 U.S.C. 154(b) by 509 days.

(21) Appl. No.: 12/550,517

(22) Filed: Aug. 31, 2009

(65) Prior Publication Data

US 2011/0047701 A1 Mar. 3, 2011

(51) Int. Cl.
*A61B 6/04* (2006.01)
*H05G 1/02* (2006.01)
(52) U.S. Cl. .......... 378/208; 378/65
(58) Field of Classification Search .......... 378/65, 378/204, 208, 209; 600/425–429
See application file for complete search history.

(56) References Cited

U.S. PATENT DOCUMENTS

| 2,552,592 A * | 5/1951 | Rush ............ 297/195.11 |
| 2006/0262898 A1* | 11/2006 | Partain et al. ............ 378/37 |
| 2010/0242177 A1* | 9/2010 | Malcolm et al. .......... 5/621 |

* cited by examiner

*Primary Examiner* — Anastasia Midkiff
(74) *Attorney, Agent, or Firm* — Dekel Patent Ltd; David Klein

(57) ABSTRACT

A system for immobilizing tissue during upright radiotherapy including a first support element and a second support element tilted with respect to each other and operative to apply pressure on opposite sides of a patient positioned therebetween so as to generally immobilize a target located in the patient, the first and second support elements being mounted on mounting members that are connected to a turntable operative to rotate the patient about a vertical rotational axis.

10 Claims, 1 Drawing Sheet

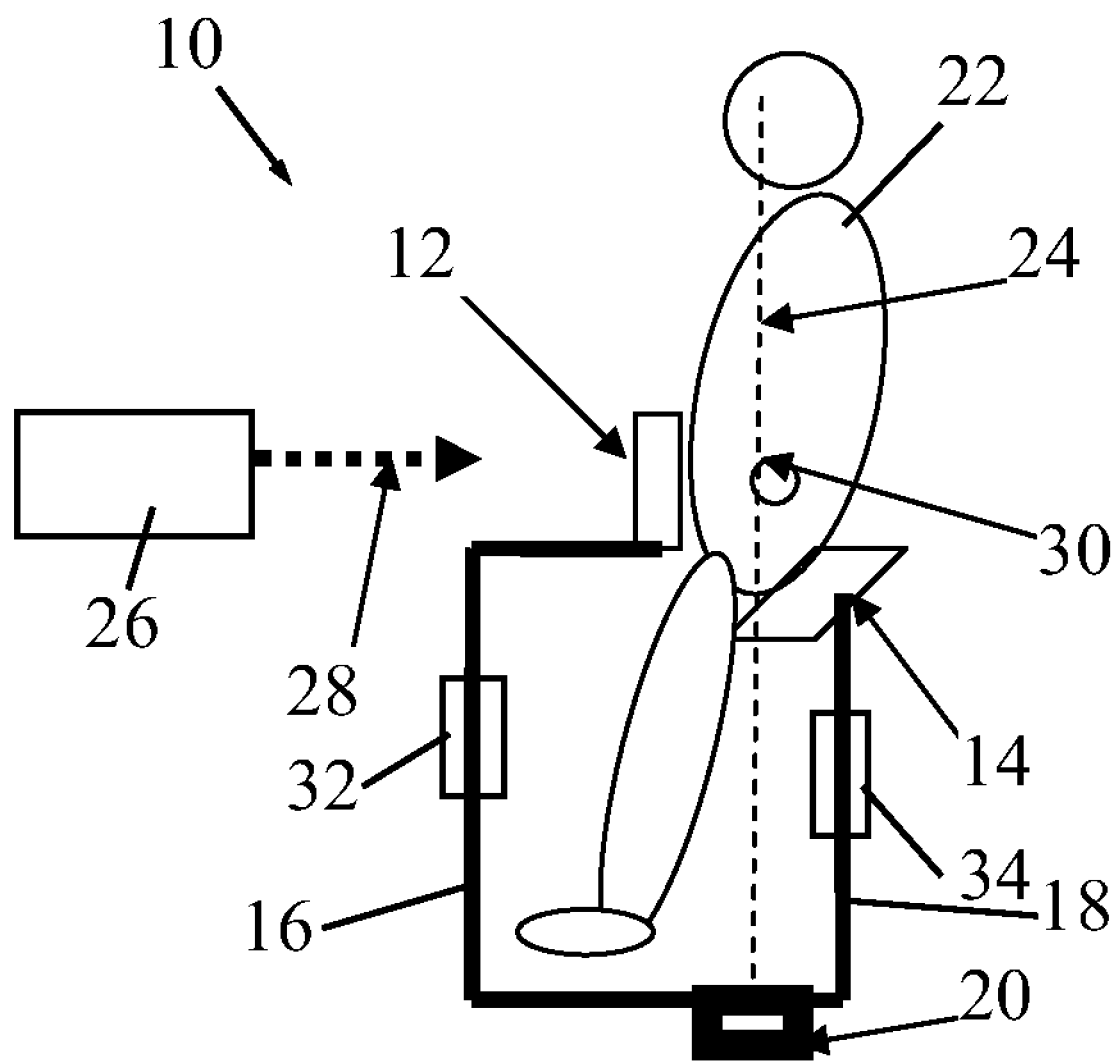

UPRIGHT RADIATION TISSUE IMMOBILIZER

FIELD OF THE INVENTION

The present invention relates generally to radiotherapy of tissues, and particularly to a system and method for immobilizing soft internal tissues (e.g., the prostate) during upright radiotherapy.

BACKGROUND OF THE INVENTION

Advanced radiotherapy requires precise imaging for treatment planning. Radiotherapy encompasses therapy, treatment and imaging (and the like), and imaging includes CT and ultrasonic imaging. Since the imaging and the treatment take place at different times and/or locations, patient positions must be maintained as identical as possible in the two procedures to reduce positional errors associated with internal organ displacement and deformation. Patient rotation about a vertical rotational axis is acceptable since such a rotation has no effect on the gravitational forces applied to the internal organs and thus no effect on organ displacement and deformation. Similarly, the patient may be translated relative to a radiation beam but remain in the same position relative to the gravitational field.

However, irradiating soft, unsupported tissues in the upright mode is not simple, due to, among other things, the problem of immobilization. For example, prostate irradiation in the upright mode incorporates positioning the prostate so as to intersect a generally horizontal and stationary radiation beam, and rotating an upright patient about a vertical rotational axis. Precise prostate positioning and immobilization relative to the beam is required. Immobilization must be both internal (the prostate relative to the pelvic boney structures) and external (the boney structures relative to the radiation beam). External immobilization of an upright patient for the duration of a treatment is a challenge as long as the patient is on his feet.

SUMMARY OF THE INVENTION

The present invention seeks to provide an improved system and method for immobilizing soft internal tissues (e.g., the prostate) during upright radiotherapy, as is described more in detail hereinbelow. Prostate treatment benefits from increased pressure applied to the pelvic tissue so as to increase internal friction and therefore increase internal prostate immobilization. Pressing the pubic area against a frontal board as a support element increases the internal pressure and provides increased friction between the pubic area and the board so as to increase external immobilization. Supporting a patient between supporting elements such that his feet are unable to cause pelvic motion further increases external immobilization.

There is provided in accordance with a non-limiting embodiment of the present invention a system for immobilizing tissue during upright radiotherapy including a first support element and a second support element tilted with respect to each other and operative to apply pressure on opposite sides of a patient positioned therebetween so as to generally immobilize a target located in the patient, the first and second support elements being mounted on mounting members that are connected to a turntable operative to rotate the patient about a vertical rotational axis.

In accordance with an embodiment of the present invention the first support element is a ventral support element and the second support element is a dorsal support element.

In accordance with an embodiment of the present invention the first support element is generally parallel (e.g., vertically positioned) with respect to the patient's body, and the second support element is tilted about a medial axis so that a top of the second support element is tilted away from a medial plane of the patient's body and a bottom of the second support element is tilted forwards towards the medial plane of the patient's body.

In accordance with an embodiment of the present invention a spacing between the first and second support elements is adjustable to allow the patient to slide down the second support element until the patient is pressed against the first support element. The mounting members can be adjusted to adjust their position (e.g., height and orientation) with respect to each other.

In accordance with an embodiment of the present invention actuators are operative to move the first and second support elements towards or away from each other to increase or decrease pressure on the patient.

There is also provided in accordance with an embodiment of the present invention a method for immobilizing tissue during upright radiotherapy including providing an immobilizer that includes a first support element and a second support element tilted with respect to each other, the first and second support elements being mounted on mounting members that are connected to a turntable operative to rotate the patient about a vertical rotational axis, supporting the patient in an upright position between the first and second support elements, applying pressure on opposite sides of the patient positioned between the first and second support elements so as to generally immobilize a target located in the patient, rotating the patient with the turntable about the vertical rotational axis, and emitting a radiation beam towards the target.

BRIEF DESCRIPTION OF THE DRAWINGS

The present invention will be understood and appreciated more fully from the following detailed description taken in conjunction with the drawings in which:

FIG. 1 is a simplified pictorial illustration of a system for immobilizing tissue during upright radiotherapy, in accordance with an embodiment of the present invention.

DETAILED DESCRIPTION OF EMBODIMENTS

Reference is now made to FIG. 1, which illustrates a system 10 for immobilizing tissue during upright radiotherapy, in accordance with a non-limiting embodiment of the present invention.

System 10 includes a first support element 12 and a second support element 14. First and second support elements 12 and 14 are tilted with respect to each other. In the illustrated embodiment, first support element 12 is a ventral (on or near the belly or front pelvic region) support element and second support element 14 is a dorsal (on or near the back pelvic region) support element. First support element 12 is generally parallel (e.g., vertically positioned) with respect to the patient's body, whereas second support element 14 is tilted about a medial axis (i.e., side-to-side axis) so that the top of second support element 14 is tilted backwards away from the patient's back (i.e., away from the medial plane of the body) and the bottom of second support element 14 is tilted forwards towards the medial plane of the body. Second support element 14 serves as seat-like sliding board tilted at an angle.

First and/or second support elements 12 and 14 are constructed of a rigid, generally radiation-transparent material, such as a suitable wood or plastic. First and second support elements 12 and 14 are mounted on mounting members 16 and 18, respectively, which are connected to a turntable 20. Mounting members 16 and 18 may be adjustable to adjust their position (e.g., height and orientation) for each patient.

A patient 22 is supported in the upright position between first and second support elements 12 and 14. Turntable 20 rotates patient 22 about a rotational axis 24. A radiation source 26 emits a radiation beam 28 towards a target 30, such as the prostate or other soft tissue. The spacing between first and second support elements 12 and 14 is adjusted to allow patient 22 to slide down the sliding board (second support element 14) until pressed against the front board (first support element 12).

First support element 12, being rigid, applies significant horizontal pressure on the frontal boney structures of the generally upright patient 22. The horizontal pressure provides external immobilization of the area of target 30. Internal immobilization is accomplished by increasing the pelvic internal pressure so as to squeeze the organs toward each other and toward the boney structures. The internal pressure and the horizontal pressure are accomplished by squeezing or wedging the portion of the patient 22 with the target 30 between first and second support elements 12 and 14. The tendency of the patient 30 to slide due to gravitational forces provides a horizontal force component by the tilted second support element 14, in the order of magnitude equal to half the patient's weight. This horizontal force pushes the pelvis toward the radiation-transparent board and increases the internal pressure. In this manner, system 10 helps immobilize the soft tissue (target 30).

Optionally, actuators 32 and 34 may be provided for deliberately moving first and second support elements 12 and 14 towards or away from each other to increase or decrease the pressure on the internal organs caused by the patient's own weight being wedged between first and second support elements 12 and 14.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A system for immobilizing tissue during upright radiotherapy comprising:

a first support element and a second support element tilted with respect to each other and operative to apply pressure on opposite sides of a patient positioned therebetween so as to generally immobilize a target located in the patient, said first and second support elements being mounted on mounting members that are connected to a turntable operative to rotate the patient about a vertical rotational axis.

2. The system according to claim 1, wherein said first support element is a ventral support element and said second support element is a dorsal support element.

3. The system according to claim 1, wherein said first support element is generally parallel to the patient's body, and said second support element is tilted about a medial axis so that a top of said second support element is tilted away from a medial plane of the patient's body and a bottom of said second support element is tilted forwards towards the medial plane of the patient's body.

4. The system according to claim 1, wherein a spacing between said first and second support elements is adjustable to allow the patient to slide down said second support element until the patient is pressed against said first support element.

5. The system according to claim 1, wherein said mounting members are adjustable to adjust their position.

6. The system according to claim 1, wherein at least one of said first and second support elements is constructed of a rigid, generally radiation-transparent material.

7. The system according to claim 1, further comprising a radiation source operative to emit a radiation beam towards said target.

8. The system according to claim 1, further comprising actuators operative to move said first and second support elements.

9. A method for immobilizing tissue during upright radiotherapy comprising:

providing an immobilizer that comprises a first support element and a second support element tilted with respect to each other, said first and second support elements being mounted on mounting members that are connected to a turntable operative to rotate the patient about a vertical rotational axis;

supporting the patient in an upright position between said first and second support elements;

applying pressure on opposite sides of the patient positioned between said first and second support elements so as to generally immobilize a target located in the patient; and rotating the patient with said turntable about said vertical rotational axis.

10. The method according to claim 9, comprising adjusting a spacing between said first and second support elements to allow the patient to slide down said second support element until the patient is pressed against said first support element.

* * * * *